US008187805B2

(12) United States Patent
Matsuhisa et al.

(10) Patent No.: US 8,187,805 B2
(45) Date of Patent: May 29, 2012

(54) METHOD OF DETECTING NUCLEIC ACID AND UTILIZATION THEREOF

(75) Inventors: Akio Matsuhisa, Osaka (JP); Seiji Yamamoto, Osaka (JP); Souji Eda, Kyoto (JP); Shinji Yamasaki, Osaka (JP)

(73) Assignee: FUSO Pharmaceutical Industries, Ltd. (JP)

( * ) Notice: Subject to any disclaimer, the term of this patent is extended or adjusted under 35 U.S.C. 154(b) by 334 days.

(21) Appl. No.: 10/588,597

(22) PCT Filed: Feb. 8, 2005

(86) PCT No.: PCT/JP2005/001840
§ 371 (c)(1),
(2), (4) Date: Feb. 4, 2007

(87) PCT Pub. No.: WO2005/075680
PCT Pub. Date: Aug. 18, 2005

(65) Prior Publication Data
US 2007/0111212 A1    May 17, 2007

(30) Foreign Application Priority Data
Feb. 9, 2004 (JP) .................................. 2004-032617

(51) Int. Cl.
*C12Q 1/68* (2006.01)
(52) U.S. Cl. ......................................................... 435/6.1
(58) Field of Classification Search .................... None
See application file for complete search history.

(56) References Cited

U.S. PATENT DOCUMENTS

| | | | | |
|---|---|---|---|---|
| 5,264,343 | A * | 11/1993 | Krystosek et al. ................. | 435/6 |
| 5,358,846 | A   | 10/1994 | Ohno et al. | |
| 5,589,333 | A * | 12/1996 | Bagasra et al. .................... | 435/6 |
| 5,746,975 | A   | 5/1998  | Chateau | |
| 5,776,679 | A * | 7/1998  | Villeponteau et al. ............ | 435/6 |
| 5,856,145 | A * | 1/1999  | Down et al. .................. | 435/91.2 |
| 5,888,733 | A * | 3/1999  | Hyldig-Nielsen et al. ........ | 435/6 |
| 5,916,526 | A   | 6/1999  | Robbins | |
| 5,939,251 | A * | 8/1999  | Hu ................................... | 435/4 |
| 6,087,134 | A * | 7/2000  | Saunders ...................... | 435/91.2 |
| 6,103,192 | A * | 8/2000  | Stapleton et al. ............... | 422/50 |
| 6,228,634 | B1* | 5/2001  | Blumenfeld et al. ...... | 435/286.1 |
| 6,448,014 | B2* | 9/2002  | Cloyd et al. ........................ | 435/6 |
| 6,599,711 | B2* | 7/2003  | Crouch et al. .................. | 435/15 |
| 6,703,247 | B1* | 3/2004  | Chu .............................. | 436/180 |
| 7,186,507 | B2* | 3/2007  | Bacallao et al. .................. | 435/6 |
| 2003/0073081 | A1 | 4/2003 | Mukai et al. | |

FOREIGN PATENT DOCUMENTS

| | | |
|---|---|---|
| CA | 2447750 | 12/2002 |
| EP | 0542301 | 5/1993 |
| EP | 1045038 A1 | 10/2000 |
| JP | 05-142122 | 6/1993 |
| JP | 08-173192 | 9/1996 |
| JP | 10-136999 | 5/1998 |
| JP | 2003-325181 | 11/2003 |
| KR | 10-2001-0021753 | 4/2001 |
| WO | WO89/10411 | 11/1989 |
| WO | WO 97/11196 | 3/1997 |
| WO | WO 97/26324 | 7/1997 |
| WO | 00/38838 | 7/2000 |
| WO | 01-081541 | 11/2001 |
| WO | WO02/099133 | 12/2002 |

OTHER PUBLICATIONS

Koltai et al., "High Throughput Cellular Localization of Specific Plant mRNAs by Liquid-Phrase in Situ Reverse Transcription-Polymerase Chain Reaction of Tissue Sections," Plant Physiology, Aug. 2000, Voo.123, pp. 1203-1212.*
Nuovo et al. (Genome Res. 1993 2: 305-312).*
Maki, Hisaji, "PCR Tips—Techniques and Hints for Mastering PCR", Shujunsha, Oct. 30, 1999.
Hames, B. David, "Gene Transcription: A Practical Approach", Medical Science International, Jul. 31, 1996.
Matsuhisa, Akio et al., "Clinical Utility of in situ hybridization method for the diagnosis of sepsis", BIO Clinica 14(1), 1999, pp. 97-101.
Sambrook, Joseph et al., "Molecular Cloning, A Laboratory Manual", Chapter 8, Third Ed., vol. 2, Cold Spring Harbor Laboratory Press, 2001.
Notomi, Tsugunori et al., "Loop-mediated isothermal amplification of DNA", Nucleic Acids Research, 2000, vol. 28, No. 12, pp. i-vii.
Lizardi, Paul M. et al., "Mutation detection and single-molecule counting using isothermal rolling-circle amplification", Nature Genetics, vol. 19, Jul. 1998, pp. 225-232.
Kricka et al., Microchip PCR, Anal. Bioanal. Chem., 377:820-825, 2003.
Trau et al., Genotyping on a Complementary Metal Oxide Semiconductor Silicon Polymerase Chain Reaction Chip with Integrated DNA Microarray, Anal. Chem. 74: 3168-3173, 2002.
Gabig et al., An introduction to DNA chips: principles, technology, applications and analysis, Acta Biochimica Polonica, 48: 615-622, 2001.
Office Action for Corresponding Korean Patent Application No. 10-2006-7017467, mailed Aug. 21, 2007, and English Translation.
Corrected Search Report mailed Feb. 28, 2008 for European Patent Application No. 05709892.3
Corning Science Products, Drug Discovery and Genomics, Catalog, 1998, pp. 28-30.

(Continued)

*Primary Examiner* — Christopher M. Babic
(74) *Attorney, Agent, or Firm* — Sheridan Ross P.C.

(57) ABSTRACT

It is intended to provide a method of detecting a nucleic acid whereby a target nucleic acid can be accurately and quickly detected at an elevated detection sensitivity compared with the existing methods; and a gene detection kit with the use of this method. A sample containing cells is fixed to a support and nucleic acids are amplified on the support as such. Then, a nucleic acid thus amplified is detected. Since the nucleic acids are not detected from the sample in this method, a lowering in the detection sensitivity due to the nucleic acid loss in the step of extracting the nucleic acids can be prevented. Since the amplified nucleic acid is detected, furthermore, detection can be made even though the nucleic acid is contained only in a trace amount in the sample.

20 Claims, 3 Drawing Sheets

OTHER PUBLICATIONS

Lodish et al., Molecular cell Biology, 4th Edition, P229, Fig 7-22, URL: http://ncbi.nlm.nih.gov/books/bv.fcgi?rid=mcb.figgrp.1649.

Office Action mailed Jan. 29, 2008 by the Australian Patent Office for Australian Patent Application No. 2005210362.

European Office Action for European Patent Application No. 05709892.3, mailed Apr. 15, 2009, 5 pages.

Cheng et al. "Chip PCR. II. Investigation of different PCR amplification systems in microfabricated silicon-glass chips," Nucleic Acids Research, 1996, vol. 24, No. 2, pp. 380-385.

EPICENTER Forum, "Direct PCR from dried blood without DNA extraction using the FailSafe™ PCR System," pp. 4-6, date unknown.

McCusker, "Improved method for direct PCR amplification from whole blood," Nucleic Acids Research, 1992, vol. 20, No. 24, 1 page.

Nordvag et al. "Direct PCR of Washed Blood Cells," BioFeedback, vol. 12, No. 4, 1992, pp. 490-492.

Ravel et al. "A highly sensitive and rapid procedure for direct PCR detection of Leishmania infantum within human peripheral blood mononuclear cells," Acta Tropica, 59 (1995) 187-196.

European Office Action for European Patent Application No. 05709892.3 mailed Sep. 11, 2009.

PCT International Search Report dated Mar. 15, 2005, for PCT Application No. PCT/JP2005/001840.

International Preliminary Report on Patentability for International (PCT) Application No. PCT/JP2005/001840, dated Aug. 9, 2006.

Grunenwald, H. "Direct PCR from Dried Blood without DNA Extraction Using the Failsafe™ PCR System", Epicenter Forum, vol. 8, Nov. 2, 2001, pp. 4-6 www.epicentre.com.

McCusker, et al. "Improved method for direct PCR amplification from whole blood," Nucleic Acids Research, 1992, vol. 20, No. 24, 1 page (pp. 6747).

Nordvag et al. "Direct PCR of Washed Blood Cells," BioTechniques, vol. 12, No. 4, 1992, pp. 490-492.

* cited by examiner

Fig. 3

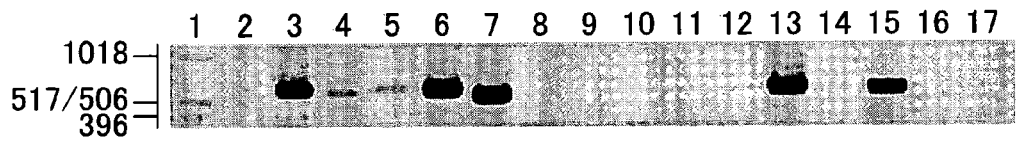

LANE 1 ; MOLECULAR WEIGHT MARKER
LANE 3-7 ; POSITIVE CONTROL
LANE 8-12 ; NEGATIVE CONTROL
LANE 13-17 ; CLINICAL SAMPLE
LANE 3, 8, 13 ; SA IDENTIFYING PRIMERS
LANE 4, 9, 14 ; SE IDENTIFYING PRIMERS
LANE 5, 10, 15 ; PA IDENTIFYING PRIMERS
LANE 6, 11, 16 ; EF IDENTIFYING PRIMERS
LANE 7, 12, 17 ; EC IDENTIFYING PRIMERS

Fig. 4

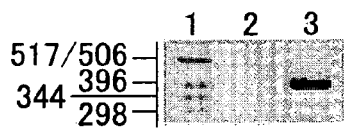

LANE 1 ; MOLECULAR WEIGHT MARKER
LANE 2 ; SEPTIC BLOOD MODEL SUPPLEMENTED WITH PBS (NEGATIVE CONTROL)
LANE 3 ; SEPTIC BLOOD MODEL SUPPLEMENTED WITH E. Coli (EC)

SEQUENCE LISTING

```
<160> NUMBER OF SEQ ID NOS: 32

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 1
gaggatgcag cgaattaaac aacgtactgc tgttcaacgc                              40

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized Primer Sequenc

<400> SEQUENCE: 2
aatgaaactt taccaacaat ttggtcttca tcaatgaggc                              40

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequenc

<400> SEQUENCE: 3
tgttcaacgc ttgattagtt ttatt                                             25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 4
tcaatgaggc caaacgcacg gctat                                             25

<210> SEQ ID NO 5
```

```
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 5
actggaataa tcattggtat tattgcttta attctagtaa                              40

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6
ctaacaaaat ctaagtagag tttcaggaat ttttctggtt                              40

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7
attctagtaa ttatgcaagg gtttc                                              25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
ttttctggtt cctcgatatg tggtg                                              25

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9
accttgccga tgatcaggtc gagcagcagc agttccgccg                              40

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
gtgttcaccg gctccaccga ggtcggcaag tacttcatgc                              40

<210> SEQ ID NO 11
<211> LENGTH: 25
<212> TYPE: DNA
```

```
<213> ORGANISM: Artificial Sequence
<220> FEATURE:
<223> OTHER INFORMATION: Description of Artificial Sequence:Artificially
      Synthesized Primer Sequence

<400> SEQUENCE: 11
agttccgccg agagggcgaa catcg                                           25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 12
tacttcatgc agtattccgc gcaat                                           25

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
cttttgctag ttcatgttta ttgatttttc gttcgattat                           40

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
taccatttct tgcatgctca tttctcctta ctactgaaac                           40

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 15
gttcgattat cccacaagat tatat                                           25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 16
ctactgaaac atcgtcttaa aaaaa                                           25

<210> SEQ ID NO 17
<211> LENGTH: 40
<212> TYPE: DNA
<213> ORGANISM: Artificial Sequence
<220> FEATURE:
```

```
<223> OTHER INFORMATION: Description of Artificial Sequence:Artificially
      Synthesized Primer Sequence

<400> SEQUENCE: 17
catttgtgaa tgagatgcac tgactaaatc aattggcccc                            40

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 18
ccgagatggg cttcacctgt ctgcgtattt ccattgcctg                            40

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 19
aattggcccc caactggtgt acccc                                            25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 20
ccattgcctg ggcgcgaatt ttccc                                            25

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 21
actgttcgta caaacttttg taatagttgg tcatg                                 35

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 22
ctcgccatct ttcaaagttg gatccattga ttcac                                 35

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence:
      Artificially Synthesized Primer Sequence
```

```
<400> SEQUENCE: 23
ggtatataaa tgactaaagg gaggtgccaa gatga                              35

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 24
gcaatgcacg tactgcaatt gcactttctt ccggag                             36

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 25
attcgatcgt cctcttgttg tcgttatcgg catcg                              35

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 26
tggtggagcg ttcgatccac gacgagttcg tcgag                              35

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 27
atcaggcgta tccattattg gattaaccac gattg                              35

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 28
ttgctcctga cgatattcac gattccctaa aatcc                              35

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 29
```

```
agatgcggat tggggatcat attcagtatg ttgcc                              35

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 30
gatcacttcg aacattacgc ccgcacggtc tttac                              35

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 31
atgaactcct tctccacaag cgccttcgg                                     29

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 32
attctttgcc ttttctgca ggaactggat                                     30
```

METHOD OF DETECTING NUCLEIC ACID AND UTILIZATION THEREOF

CROSS REFERENCE TO RELATED APPLICATION

This application is a national stage application under 35 U.S.C. 371 of PCT Application No. PCT/JP2005/001840 having an international filing date of Feb. 8, 2005, which designated the United States, which PCT application claimed the benefit of Japan Application Serial No. 32617/2004, filed Feb. 9, 2004, the entire disclosure of which are hereby incorporated herein by reference.

TECHNICAL FIELD

The present invention relates to a nucleic acid detection method and use thereof. More specifically, the invention relates to a method for efficiently amplifying a trace amount of nucleic acid in a sample and accurately and quickly detecting it, and a gene detecting kit using such method.

BACKGROUND ART

In order to find a specific nucleic acid or gene, a method is commonly employed that amplifies a target nucleic acid or gene and detects the product of amplification. As the methods that specifically amplify a target nucleic acid or gene, the following methods are known. PCR method (see Non-Patent Documents 1 and 2, for example), RT-PCR method (see Non-Patent Documents 1 and 2, for example), ICAN method (see Patent Document 1, for example), LAMP method (see Non-Patent Document 3, for example), RCA method (see Non-Patent Document 4, for example), and primer extension method (see Non-Patent Document 5, for example). Among these examples, PCR and RT-PCR are most commonly used. In these methods, short nucleic acid sequences including the base sequence of the target nucleic acid are used as primers, and a template-specific nucleic acid synthesizing reaction is performed in vitro, using DNA polymerase or RNA polymerase.

If the amplified nucleic acid fragments were labeled by suitable methods during or after the amplification reaction, these nucleic acid amplification methods are able to detect even a trace amount of nucleic acid in a sample. Other known examples include DNA microarray (macroarray) method and differential display method. For the detection of nucleic acid, these methods use primers of random base sequences to non-specifically amplify and label the nucleic acids. Recently, DNA microarray has caught a particular attention for its ability to comprehensively detect genes that are associated with various types of diseases.

In addition to these nucleic acid amplification methods, ISH (in situ hybridization) method and FISH (fluorescein in situ hybridization) method are available. In order to find a specific nucleic acid or gene, these methods cause a target nucleic acid in tissues or cells to hybridize with probes, for which labeled nucleic acids having the complementary base sequences are used (see Non-Patent Document 1, for example). ISH method is widely used to detect expression of specific genes in tissues, or compare expression levels of specific genes in tissues. FISH method is widely used to find specific gene regions on the chromosomes.

Another example is in situ PCR method. This method employs PCR to amplify the target nucleic acid, uses ISH to cause hybridization with probes, and detects the target nucleic acid with a microscope (see Non-Patent Document 2, for example). However, owning to difficulties in setting optimum reaction conditions, the method suffers from poor reproducibility and is not pervasive.

Applicant of the present invention has been marketing "HYBRISEP®", which is a bacteria detecting kit for detecting bacteria in peripheral blood white blood cells according to the ISH method (in vitro diagnostic drug (Approval Number: AMZ00620000)). "HYBRISEP®" has come under the spotlight in the field of infection, because it is able to detect bacteria at about 4 times more sensitivity than conventional blood culture methods and thereby complete the test within a day, instead of at least 3 days conventionally required (see Non-Patent Document 6, for example). Further, Applicant has proposed a method for detecting and identifying foreign microbes phagocytosed by phagocytes (see Patent Document 2, for example), and improvement of the method (see Patent Document 3, for example). "HYBRISEP®" was developed based on these inventions.

[Patent Document 1]
Japanese Patent No. 3433929 (registered on May 30, 2003, issued on Aug. 4, 2003)
[Patent Document 2]
International Publication WO89/10411 (published on Nov. 2, 1989, corresponding patent: Examined Patent Publication No. 07-40)
[Patent Document 3]
International Publication WO02/099133 (published on Dec. 12, 2002)
[Non-Patent Document 1]
J. Sambrook et al. "Molecular Cloning, A Laboratory Manual, Third Edition" Cold Spring Harbor Laboratory (2001)
[Non-Patent Document 2]
Hisaji Maki, "PCR Tips-Techniques and Hints for Mastering PCR-, Shujunsha, 1999
[Non-Patent Document 3]
Tsugunori Notomi et al. Loop-mediated isothermal amplification of DNA. Nucleic Acids Research, vol. 28, No. 12: e63 (2000)
[Non-Patent Document 4]
Lizardi P M et al. Mutation detection and single-molecule counting using isothermal rolling-circle amplification. Nature Genetics, July; 19(3):225-32. (1998)
[Non-Patent Document 5]
B. D. Hames, S. J. Higgins: Translation by Masami Horikoshi, "Gene Expression and Transcription Factors", Medical Science International, 1996
[Non-Patent Document 6]
Akio Matsuhisa, Hiromasa Araki, "Clinical Use of In Situ Hybridization in Sepsis Diagnosis", BIO Clinica, Hokuryukan, 1999, Vol. 14, No. 1, p. 97-101

While the foregoing nucleic acid amplifying methods such as PCR and hybridization methods such as ISH are used to detect specific nucleic acids or genes, the methods may not be able to provide enough detection sensitivity, reproducibility, or convenience, etc., when the sample contains only a trace amount of target nucleic acid or gene.

In the nucleic acid amplifying method such as PCR, nucleic acids need to be extracted from the sample. In this process, it is difficult to extract the nucleic acids without any loss. For example, there are cases where the amount of nucleic acid collected from the sample may not be sufficient to provide a template due to a loss in the extracting procedure, even when the sample contains a sufficient amount of target nucleic acid to be used as a template for amplification. In such case, the target nucleic acid may not be amplified sufficiently due to reduced amplification efficiency, with the result that the target nucleic acid in the sample cannot be detected. In this case, the result is false negative and inaccurate. Further, even the same sample may yield different results depending on how much nucleic acid is lost in the extracting procedure. This works against reproducibility. The problem of nucleic acid amplifying method that requires extraction of nucleic acids, then, is that a loss of nucleic acid in the nucleic acid extracting procedure may lead to reduction of amplification efficiency and detection sensitivity when the sample contains only a trace amount of target nucleic acid.

Further, when the reagent contains substances that inhibit amplification reaction (for example, heparin, detergent, protein denaturing agent, organic solvent, etc.), the problem of reduced amplification efficiency and detection sensitivity may also occur.

As for the hybridization method such as ISH, the method does not require extraction of nucleic acid and there accordingly will be no loss of nucleic acid. However, when the sample contains only a trace amount of target nucleic acid, there is a difficulty in detecting probe nucleic acids that have hybridized with the target nucleic acid.

While "HYBRISEP®" developed by the Applicant of the present invention enables accurate and quick detection of bacteria in peripheral blood white blood cells according to the ISH method, it has the following drawbacks.

(1) Certain skill is required because signaling of the cells is observed by naked eyes through a microscope.

(2) Detection rate is reduced in clinical samples obtained from patients with a reduced number of white blood cells, because the "HYBRISEP®" detects only those bacteria phagocytosed by the white blood cells.

The present invention was made in view of the foregoing problems, and an object of the present invention is to provide a nucleic acid detection method that can accurately and quickly detect a target nucleic acid even when a sample contains only a trace amount of target nucleic acid.

DISCLOSURE OF INVENTION

The inventors of the present invention diligently worked to solve the foregoing problems, and found that a target nucleic acid in a sample could be accurately and quickly detected if a sample were fixed on a support and the nucleic acids were amplified on the support without having been extracted from the sample. This was accomplished without lowering detection sensitivity due to a loss of nucleic acids in the sample. The present invention was made based on this finding. Specifically, the present invention provides:

(1) A nucleic acid detection method including: a sample fixing step of fixing a cell-containing sample on a support; a nucleic acid amplifying step of amplifying sample's nucleic acids on the support; and a determining step of determining whether the amplified nucleic acids contain a target nucleic acid.

(2) A nucleic acid detection method as set forth in (1), further including, before the nucleic acid amplifying step, a nucleic acid exposing step of exposing sample's nucleic acids.

(3) A nucleic acid detection method as set forth in (2), wherein the nucleic acid exposing step is performed by one or more methods selected from the group consisting of a detergent treatment method, an enzyme treatment method, and a heat treatment method.

(4) A nucleic acid detection method as set forth in any one of (1) through (3), wherein the nucleic acid amplifying step is performed by PCR (polymerase chain reaction).

(5) A nucleic acid detection method as set forth in any one of (1) through (4), wherein the amplified nucleic acids are labeled in the nucleic acid amplifying step.

(6) A nucleic acid detection method as set forth in (5), wherein, in the determining step, a target nucleic acid is detected if there is complementary hybridization of known gene fragments with probes, for which the nucleic acids amplified and labeled in the nucleic acid amplifying step are used.

(7) A nucleic acid detection method as set forth in (6), wherein the known gene fragments are fixed on the support in advance.

(8) A nucleic acid detection method as set forth in (5), wherein, in the determining step, a target nucleic acid is detected with use of a DNA microarray and probes, for which the nucleic acids amplified and labeled in the nucleic acid amplifying step are used.

(9) A nucleic acid detection method as set forth in any one of (1) through (8), wherein the sample originates in biological sources.

(10) A nucleic acid detection method as set forth in (9), wherein the biological sample originates in humans.

(11) A gene detecting kit for detecting a target gene in a sample according to a nucleic acid detection method of any one of (1) through (10).

(12) A gene detecting kit for detecting a disease-associated gene of humans according to a nucleic acid detection method of (10).

(13) A gene detecting kit as set forth in (12), wherein the disease-associated gene of humans is a gene of infection-causing microbes that have infected humans.

(14) A gene detecting kit as set forth in (13), wherein the gene of infection-causing microbes that have infected humans is a drug-resistant gene.

(15) A gene detecting kit as set forth in (13), wherein the gene of infection-causing microbes that have infected humans is a drug-sensitive gene.

(16) A gene detecting kit as set forth in (12), wherein the disease-associated gene of humans is a marker gene for cancer.

(17) A gene detecting kit as set forth in (12), wherein the disease-associated gene of humans is a genetic disease-associated gene.

(18) A gene detecting kit as set forth in any one of (II) through (17), which includes: a target gene amplifying primer; PCR reaction buffer; a mixture of deoxynucleoside triphosphate; labeled deoxynucleoside triphosphate; thermostable DNA polymerase; a sample-fixing support; and an indicator for detecting amplified nucleic acids.

According to the foregoing configurations, there will be almost no loss during the extraction procedure of nucleic acids even when a sample contains only a trace amount of target nucleic acid, and as a result the target nucleic acid can be detected with superior sensitivity, accuracy, and reproducibility. Further, the detection is convenient and quick, and does not require skill to yield results.

Additional objects, features, and strengths of the present invention will be made clear by the description below. Further, the advantages of the present invention will be evident from the following explanation in reference to the drawings.

BRIEF DESCRIPTION OF DRAWINGS

FIG. 3 is an electrophoretic image showing microbes phagocytosed by the white blood cells, as detected by a nucleic acid detection method of the present invention performed on clinical samples obtained from patients suffering from sepsis.

FIG. 4 is an electrophoretic image showing increased expression levels of IL6 in the white blood cells, as detected by a nucleic acid detection method of the present invention performed on a septic blood model.

BEST MODE FOR CARRYING OUT THE INVENTION

The following will describe one embodiment of the present invention. It should be noted that the invention is not limited in any way by the following description.

1. A Nucleic Acid Detection Method According to the Present Invention

Figure 1:
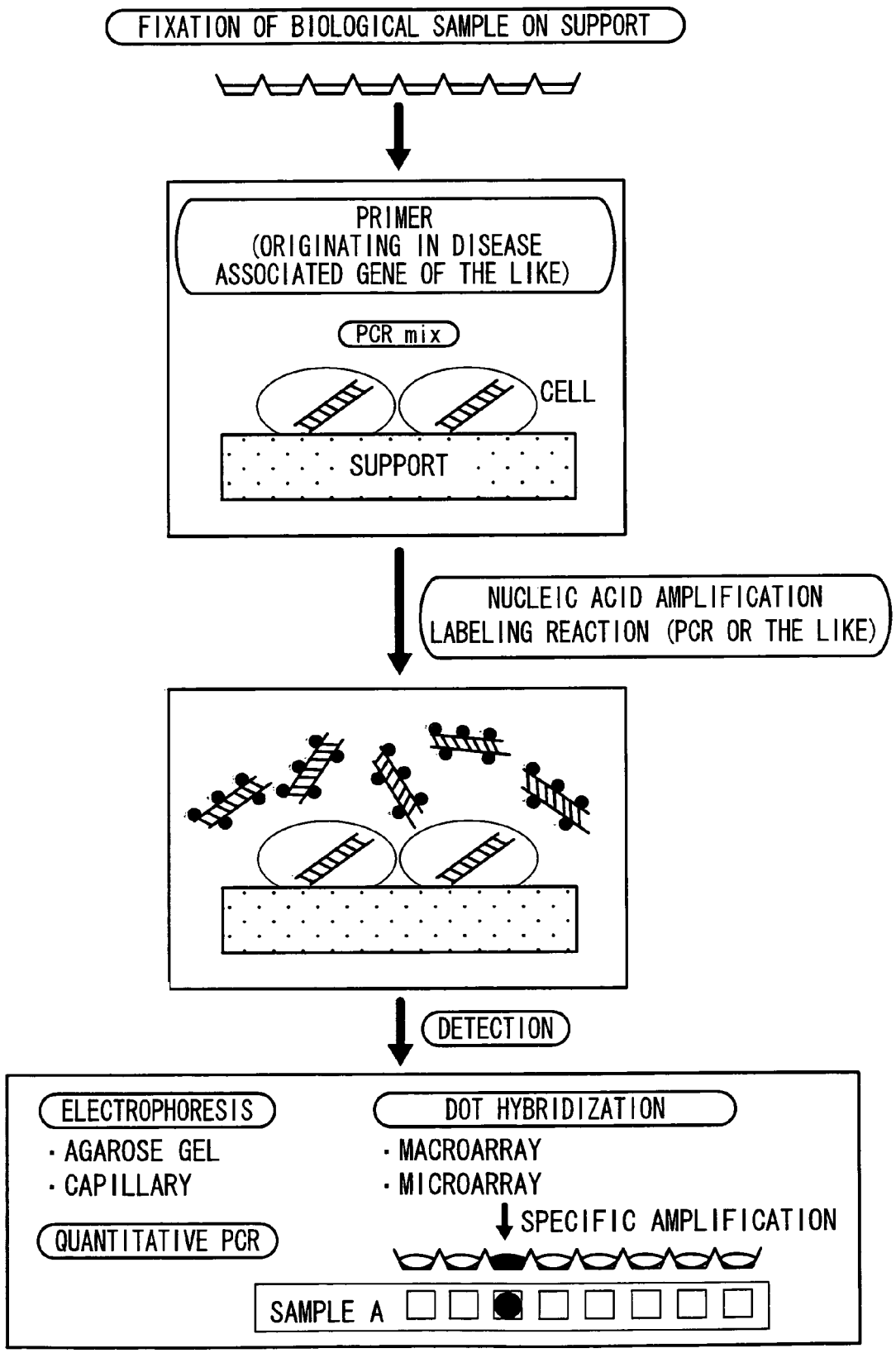
FIG. 1 is a diagram showing an example of a nucleic acid detection method according to the present invention.

A nucleic acid detection method according to the present invention includes: a sample fixing step of fixing a cell-containing sample on a support; a nucleic acid amplifying step of amplifying sample's nucleic acids on the support; and a determining step of determining whether the amplified nucleic acids contain a target nucleic acid. Optionally, a nucleic acid exposing step of exposing sample's nucleic acids may be included as a preceding step of the nucleic acid amplifying step. FIG. 1 illustrates one embodiment of a nucleic acid detection method of the present invention. In the embodiment shown in FIG. 1, a biological sample is fixed on a support (sample fixing step), and PCR is performed by adding a PCR mixture containing primers originating in disease-associated genes (nucleic acid amplifying step). In the nucleic acid amplifying step, the amplified nucleic acids are labeled during or after the amplification (details will be described later). In the final step, it is determined whether the amplified nucleic acids contain a target nucleic acid, using nucleic acid detecting means such as electrophoresis (agarose gel electrophoresis, capillary electrophoresis, etc.), quantitative PCR, dot hybridization (macroarray, microarray, etc.) (determining step). It should be noted, however, that a nucleic acid detection method according to the present invention is not just limited to the embodiment shown in FIG. 1. The following will describe features of the nucleic acid detection method in detail.

(1) Sample Fixing Step

In the sample fixing step, a sample is fixed on a support. Since a sample is fixed on a support, a nucleic acid purifying step usually performed for the amplification and labeling of nucleic acids can be omitted. Further, fixing a sample on a support allows for easy removal of amplification inhibitors even when the sample solution contains amplification inhibitors, for example, such as heparin, EDTA-2Na, cation, a high concentration protein solution, a high concentration salt solution, a detergent-containing solution, a protein denaturing solution (urea, guanidine HCl, etc.), and an organic solvent, because these amplification inhibitors usually do not stay in the cells. Further, with the sample fixed on a support, the nucleic acids can be stably preserved.

[Sample]

The sample used in a nucleic acid detection method of the present invention (hereinafter, may be referred to simply as "present detection method") is not particularly limited as long as it includes cells. The target nucleic acid detected by the present detection method may be DNA (deoxyribonucleic acid) or RNA (ribonucleic acid). Since cells include nucleic acids (DNA and RNA), a target nucleic acid in the cells can be detected by the present detection method. The type of cell is not particularly limited and any cell can be used, including, for example, animal cells, plant cells, and microbes. The non-cellular component of the sample needs to be digestible by a chemical treatment, enzyme treatment, heating, or the like in the nucleic acid exposing step (described later), so that the nucleic acids in the cells can be exposed by these treatments. Preferably, the present detection method uses biological samples containing cells. However, the present detection method is not limited to this particular example and is applicable to non-biological samples as well.

A non-biological sample may be, for example, food, soil, water, fiber, or dust, with cells. Preferable examples of biological samples are biological constituents of animals and plants. Examples of samples originating in humans and other animals include: body fluids such as blood, tissue fluid, lymph fluid, cerebrospinal fluid, pus, mucus, snot, sputum, urine, crap, and ascites fluid; tissues such as skin, lungs, kidneys, mucous, and various other organs and bones; and washed solution of nasal cavity, bronchi, skin, and various other organs and bones. Further, a dialysate fluid of humans can also be used as a sample.

The target nucleic acid of the present detection method is not just limited to the nucleic acids of the cells contained in the sample. For example, the present detection method is also applicable to nucleic acids of viruses that have infected the cells, or nucleic acids of microbes phagocytosed by cells. Thus, biological samples including the phagocytes (e.g., white blood cells) of patients suffering from an infectious disease can suitably be used in the present detection method.

[Support]

The support is used to fix the sample on its surface and amplify the target nucleic acid of the sample thereon. So long as the support serves to meet this purpose, the material or shape of the support is not particularly limited. For example, the support may be made of glass, metal, synthetic resin (polystyrene, polyethylene, polypropylene, polyvinyl chloride, polyester, polyacrylic ester, nylon, polyacetal, fluorocarbon resin, etc.), polysaccharides (cellulose, agarose, etc.), and filter paper. As for the shape, the support may be a plate, tray, sphere, fiber, rod, board, container, cell, or tube, for example. A suitable shape is selected according to the conditions by which the present detection method is performed.

The support may be provided for the number of samples used, corresponding to each type of sample. However, for improved efficiency, it is more preferable that more than one kind of sample be fixed on a single support. The present detection method performs the sample fixing step and the nucleic acid amplifying step (or the sample fixing step, the nucleic acid exposing step, and the nucleic acid amplifying step) as a series of procedures. It is therefore required to prevent the samples from mixing together, when more than one kind of sample is fixed on a single support. As such, it is preferable that the support used in the present detection method be divided into a plurality of compartments. Further, in the case where the nucleic acid amplifying step of the present detection method employs PCR to amplify nucleic acids, it is preferable that the support be made of a thermostable material. It is particularly preferable that the support be shaped to fit a commercially available gene amplifier for PCR (thermal cycler).

[Fixation]

As used in the context of a nucleic acid detection method according to the present invention, the term "fix" refers to anchoring or immobilizing a sample on a support by some method. A fixation method used in the present detection method is not particularly limited, and can be suitably selected from known fixation methods. Examples of known methods include: a carrier binding method in which binding to a water-insoluble carrier is made by covalent bonding or ion bonding; a crosslinking method in which a crosslinking agent is used to form a covalent bond and the sample is insolubilized; an envelope method in which the sample is enveloped by a polymer gel or semipermeable membrane; and a dehydration method in which the protein is quickly denatured and immobilized on a carrier. More specifically, Carnoy fixation, alcohol fixation, heat fixation, glutaraldehyde fixation, dry fixation, acetone fixation, methanol fixation, and formalin fixation can be used.

The term "fix" also include bonding a sample on a surface of the support. To this end, a surface of the support may be coated with a substance that improves adhesion, for example, such as 3-aminopropyltriethoxy silane (APS), poly-L-lysine, or gelatin. By such a pre-treatment, the support can firmly anchor or immobilize the sample, though the effectiveness of the treatment varies depending on the type of sample used. This bonding procedure may be performed in addition to the fixation method as exemplified above.

(2) Nucleic Acid Exposing Step

In order for the nucleic acid amplifying step to amplify nucleic acids contained in a sample, it is necessary that the primers and nucleic acid polymerase reach the target nucleic acids. In some samples, the target nucleic acids are exposed on a sample surface. For these samples, the nucleic acid amplifying step can be performed immediately after the sample fixing step. As such, the nucleic acid exposing step is not essential in the present detection method. However, the nucleic acid exposing step does become essential and the target nucleic acids need to be exposed when the target nucleic acids are not exposed on a sample surface.

The nucleic acid exposing step can use, for example, a detergent treatment method (SDS, TRITON-X, TWEEN-20, BRIJ, NP-40, CHAPS, etc.), an enzyme treatment using protease or the like, and a heat treatment. However, the method used in the nucleic acid exposing step is not just limited to these examples, and can be suitably selected according to the type of sample and target nucleic acid. For example, in detecting genes of bacteria phagocytosed by white blood cells in sepsis caused by bacterial infection, genes of bacteria and other microbes such as fungi can be exposed with the use of enzymes, such as lysostaphin, lysozyme, N-acetylmuramidase, and zymolyase, that digest the cell walls of bacteria.

(3) Nucleic Acid Amplifying Step

In the nucleic acid amplifying step, the target nucleic acid is amplified on a support with the sample fixed thereon. A biggest feature of a nucleic acid detection method according to the present invention is that it amplifies the target nucleic acid on a support with the sample fixed thereon, without extracting or purifying the nucleic acids in the sample. Because there is no loss in the extraction and purification procedures, the target nucleic acid can be detected without lowering detection sensitivity, even when the sample contains the target nucleic acid only in a trace amount. This simplifies the procedure and reduces the time it requires.

By "amplification of nucleic acids," it is intended that nucleic acids in a sample are amplified with the use of DNA polymerase or RNA polymerase, and primers, which are specific to arbitrary portions of the sequence of the target nucleic acid or have random sequences. For amplification, known amplification methods can be used. Specific examples include a PCR method, a Nested-PCR method, a RT-PCR method, an ICAN method, a UCAN method, a LAMP method, a primer extension method, transcription, and replication.

Among the amplification methods as exemplified above, the PCR method can preferable be used in the present detection method. The following will describe the case where the PCR method is used in the nucleic acid amplifying step of the present detection method.

The PCR method is a common technique known in genetic engineering, whereby a specific DNA region is amplified by a cycle of DNA polymerize reactions in vitro, using DNA polymerase (thermostable DNA polymerase, hereinafter may be referred to as "Taq polymerase"), and two kinds of primers flanking the specific DNA region. Nested-PCR method and RT-PCR method are variations of the PCR method.

Nested-PCR is a two-stage procedure that uses a different set of primers in each stage. In this method, the first amplification product of a target region is used as a template to perform the second run, in which the second set of primers (inner primers) are placed within the primer positions of the first primers (outer primers). In this way, the second run can amplify the target nucleic acid to a detectable level even when the first run fails to amplify the target nucleic acid sufficient for detection. Further, if the first amplification yields non-specific products, it would be highly unlikely that these non-specific products would have sequences similar to the primers used in the second run. That is, the probability of amplifying only the fragments that include the target sequence is increased in the second run. This solves the problems caused by non-specific products, and enables more accurate detection of the target nucleic acid.

RT-PCR is a PCR method designed for mRNA. As a preparatory stage of PCR, the method includes a step of performing a reverse transcription reaction using reverse transcriptase. When RT-PCR is used in the present detection method, mRNA can be detected as a target nucleic acid. That is, when used with RT-PCR, the present detection method is applicable to the detection of gene expression.

As described in conjunction with the [Support] section above, the support is preferably divided into a plurality of compartments, because the present detection method performs PCR on the support with the sample fixed thereon. When using such a support, PCR follows the following procedure. First, a PCR mixture (buffer, dNTP mix, Taq polymerase, etc.) is added to the sample in each sector of the support, and then primers are added to perform PCR with a device such as a DNA amplifier (thermal cycler). As the primers, primer sets for specifically amplifying various target nucleic acids are used for each PCR. Reaction conditions, such as the amount of reaction solution, the concentrations of enzyme and substrate, and the reaction temperature are not particularly limited, and are suitable selected depending on the type of sample and nucleic acid used.

In the case of Nested-PCR, the first run is carried out on the support, and the second run is carried out with a PCR tube or the like. The primers used for the second run need to be designed at or inside the primer positions used in the first run.

It is preferable that the fragments amplified by PCR have sequences specific to the target nucleic acid. Since the majority of nucleic acids contained in the sample are non-targets, the PCR is likely to yield non-specific products if the primers were not designed for sequences specific to the target microbe. It is therefore important to know beforehand specific sequences of the target nucleic acid and design primers to amplify these specific sequence portions.

It is preferable that the length of amplified fragment be fall in a range of 50 bp to 5,000 bp, or more preferably 100 bp to 2,000 bp. Outside these ranges, the amplification may not effectively yield specific products.

In the nucleic acid amplifying step, the amplified nucleic acids are preferably labeled. This enables the subsequent determining step to be performed more efficiently. The nucleic acids may be labeled during or after amplification. A means of labeling is not particularly limited. For example, radioisotope labels, hapten (biotin, digoxigenin, etc.) labels, and fluorescent labels may be used.

When labeling is made during amplification of nucleic acids in the nucleic acid amplification method, a substrate can be used to label the target nucleic acid during the amplification reaction employing a PCR method, a Nested-PCR method, a RT-PCR method, an ICAN method, a UCAN method, a LAMP method, a primer extension method, transcription, or replication. As the substrate, a nucleotide analogue labeled with, for example, hapten (digoxigenin, biotin), FITC, or radioisotope can be used. When labeling after the amplification reaction, methods such as a nick translation method, a random prime method, a primer extension method, a TdT method, or a 5' kination method can be used. In this case, a labeled nucleotide analogue may also be used as a substrate. Alternatively, primers with labeled ends may be used as well.

When the nucleic acid amplifying step uses primers specific to arbitrary sequences of the target nucleic acid, amplification yields nucleic acid fragments of known base sequences. On the contrary, when primers of random sequences are used, the amplification, which is non-specific in this case, yields nucleic acid fragments of random sequences. When the nucleic acid amplifying step uses primers that are designed to amplify nucleic acid fragments of known base sequences, whether the amplified nucleic acids are target nucleic acids can be determined in the subsequent determining step by checking the base sequences of the fragments, or through hybridization with nucleic acid fragments of known base sequences. When primers of random sequences are used, whether the sample contains a target nucleic acid can be determined in the determining step with the use of a DNA microarray or the like.

(4) Determining Step

The determining step determines whether the nucleic acids amplified in the nucleic acid amplifying step are target nucleic acids. In a nucleic acid detection method according to the present invention, detection is made after the nucleic acids have been amplified. There accordingly will be no difficulty in detecting the target nucleic acid even when the target nucleic acid is contained only in a trace amount. Further, since the detection allows for use of known methods, no skill is required for the determination procedure.

As used herein, "determination" includes checking the length or base sequence of amplified nucleic acid fragments. The meaning of the term also includes checking RNA transcribed from the amplified DNA fragments, and checking proteins that were expressed based on the amplified nucleic acid fragments. The method used in the determining step is not specifically limited and can be suitably selected. For example, nucleic acid (DNA or RNA) may be checked by a method such as agarose gel electrophoresis, quantitative PCR, sequencing, dot hybridization, DNA microarray, Southern hybridization, or Northern hybridization. As for checking proteins, a method such as SDS-PAGE, Western blotting, or mass spectrometry (MALDI-TOF-MS, LC-MS, LC-MS/MS, etc.) may be used, for example.

Most conveniently, agarose gel electrophoresis can be used as the method of determination. In this method, the nucleic acid fragments amplified from the sample are compared in length with the nucleic acid fragments that were amplified using only the target nucleic acid as a template. However, since a match is found in this manner, the method may yield a false positive result when the amplification yields non-specific products of similar lengths by chance. A method that is most reliable for accurately finding a match between the amplified nucleic acid and target nucleic acid is the method (sequencing) that checks the base sequences of the amplified nucleic acids. This method can also be used to detect SNP (single nucleotide polymorphism).

In order to conveniently and accurately find whether the target nucleic acid has been amplified, it is preferable that the target nucleic acid be detected based on complementary hybridization of known gene fragments with probes, for which labeled amplified nucleic acids are used. In this method, it is preferable that the nucleic acids used as probes be amplified with primers that are designed to have the base sequences of the known gene fragments used for hybridization. It is also preferable that the known gene fragments used for hybridization be fixed on a support in advance. In this way, hybridization with the probes can be accurately captured. Further, since the known gene fragments on a support carry positional information, a variety of known gene fragments can be aligned on the support to detect multiple genes at once.

More specifically, for example, a target nucleic acid is first spotted (immobilized) on a nylon membrane or the like, and then hybridized with the amplified nucleic acids used as probes. If there is hybridization between the spotted nucleic acid and the amplified nucleic acids, then it can be said that the sample had contained the target nucleic acid. Hybridization does not occur when the nucleic acid amplifying step did not amplify the nucleic acid, or non-target nucleic acids were non-specifically amplified. In this case, the sample is regarded as having contained the target nucleic acid.

The known gene fragments used for hybridization are not particularly limited as long as they contain base sequence portions to be amplified in the nucleic acid amplifying step. Preferably, the known gene fragments contain only the base sequence portions to be amplified, or part of the base sequence portions to be amplified. This is to avoid undesirable hybridization, which may occur when the gene fragments include non-amplified portions and when the amplified nucleic acids are non-specific products that do not have the target sequence.

Hybridization can be carried out according to known methods. As the probes, amplified nucleic acids that have been labeled for known gene fragments can be used. For example, methods described in J. Sambrook et al., Molecular Cloning, A Laboratory Manual, Third Edition, Cold Spring Harbor Laboratory (2001) can be used. However, the method of hybridization is not just limited to this specific example.

Alternatively, the nucleic acids that are amplified and labeled in the nucleic acid amplifying step may be used as probes, and the presence or absence of target nucleic acid may be determined with the use of a DNA microarray. The DNA microarray may be of either oligo DNA type or cDNA type. The DNA microarray may be purchased or prepared. When the microarray is used in the determining step, it is possible to determine whether the target nucleic acid is present in the nucleic acids that were non-specifically amplified in the nucleic acid amplifying step with the primers of random sequence.

(5) Applicable Fields of a Nucleic Acid Detection Method of the Present Invention The present detection method is applicable to all fields of conventional diagnoses known as gene diagnoses. The following lists some of the non-limiting examples.

(a) Detection of pathogenic microbes (bacteria, fungi, viruses, parasites, etc.), i.e., molecular diagnosis of infections.
(b) Molecular diagnosis of cancer
(c) Molecular diagnosis of genetic disease before birth
(d) Molecular diagnosis of genes associated with drug metabolism
(e) Molecular diagnosis of samples in forensic medicine
(f) Molecular diagnosis of disease marker genes
(g) Tissue typing in transplantation
(h) Compatibility test
(i) SNPs detection A nucleic acid detection method according to the present invention is considered to be best suited for the molecular diagnosis of infections as set out in item (a) of the list. The following describes the reasons for this.

The probability of pathogenic microbes being present in the blood or body fluid is rather small, and these organisms cause infections upon entry into the host cells. Thus, for the detection of infection-causing pathogenic microbes, immune cells such as the white blood cell are suitably used as a sample. Conventionally, PCR or ISH is used for the detection of bacteria phagocytosed by the cells, or viruses that have entered the cells. In PCR, the nucleic acids are amplified after extraction from the cells, whereas, in ISH, the target nucleic acid is detected without amplifying the nucleic acids. While these methods have been used conventionally, they are not always sufficient when it comes to detection sensitivity, reproducibility, and convenience, etc. On the other hand, in a nucleic acid detection method according to the present invention, the cells that have phagocytosed bacteria or invaded by viruses or other microbes are directly fixed on a support, and the nucleic acids of the bacteria or viruses are amplified and detected with the cells fixed on the support. This greatly improves detection sensitivity and detection accuracy over the conventional methods.

Another conventional method that detects pathogenic microbes in the cells is in situ PCR. This method is performed according to the following procedure. First, cells are fixed on a glass slide, and PCR is performed in the cells. The amplified products in the cells are then hybridized with probes according to ISH method, and the visualized nucleic acids are detected with a microscope. While in situ PCR provides detection sensitivity that compares to detection sensitivity of a nucleic acid detection method of the present invention, the method requires tedious condition settings and falls behind in terms of reproducibility. Another drawback of the method is that it sets off many non-specific reactions, making it difficult to distinguish the non-specific products of amplification from the target specific product in the cells.

For these reasons, a nucleic acid detection method according to the present invention provides superior means of detecting bacteria phagocytosed by the cells, or viruses or other microbes that have entered the cells.

2. Gene Detection Kit According to the Present Invention

A gene detection kit according to the present invention (hereinafter, may be referred to as "present kit") is used to detect target genes in a sample with the use of a nucleic acid detection method of the present invention. The kit includes various reagents and instruments to be used in the present detection method. This enables the present detection method to be performed more easily and yield more accurate results in a shorter time period. As used herein, "genes" include both DNA and RNA.

(1) Configuration of the Present Kit

Preferably, the present kit at least includes: a support, used in the sample fixing step, for fixing samples; primers used in the nucleic acid amplifying step; nucleic acid polymerase; a substrate (nucleoside triphosphate); reagents such as a buffer; and an indicator, used in the determining step, for detecting amplified nucleic acids, among other reagents and instruments. In the case where the kit is designed for a specific sample and requires the nucleic acid exposing step, the kit may include reagents for exposing nucleic acids (detergent, protein lytic enzyme, etc.). Further, the kit may include reagents for fixing samples, depending on the type of sample used. For example, in the case where the kit is designed specifically for biological samples that includes white blood cells, and when the target nucleic acid is the genome of bacteria or other microbes that were phagocytosed by the white blood cells, the kit may include reagents for fixing samples (for example, Carnoy's fixative), and reagents for exposing nucleic acids (for example, a lytic enzyme for the cell wall of microbes).

Further, depending upon the types of nucleic acid amplification method and determination method, the kit may include specific types of reagents. For example, in the case where PCR is used for the nucleic acid amplification method, the nucleic acid amplifying step requires a PCR reaction buffer, a deoxynucleoside triphosphate mixture, and thermostable DNA polymerase (Taq polymerase). In the case where PCR requires labeling of the nucleic acids, the kit additionally includes labeled deoxynucleoside triphosphate.

In the case where agarose gel electrophoresis is used for the determination method, the kit is designed to include agarose gel, electrophoresis buffer, molecular weight markers, and reagents for staining nucleic acids, among others. In the case where dot hybridization is used for the determination method, the kit is designed to include: a target nucleic acid-spotted (immobilized) membrane; hybridization buffer; a detection indicator, which is selected according to the type of label used for the nucleic acids (for example, when digoxigenin label is used, enzyme-labeled anti-digoxigenin antibody and a substrate for imparting color to the labeled enzymes); and a hybridization bag, among other essential reagents and instruments. In the case where DNA microarray is used for the nucleic acid detection method, the kit is designed to include DNA microarray, which is selected according to the type of target nucleic acid, and various essential reagents and instruments.

That is, the kit may be designed to include various types of reagents and instruments in different combinations, depending upon the types of samples, target genes, nucleic acid amplification method, and nucleic acid detection method. Accordingly, the constituents of the present kit are not just limited to the reagents and instruments exemplified above. Rather, various types of known reagents and instruments may be appropriately selected and included in the kit depending on intended use.

(2) Target Genes

More than one target gene may be included in the kit. By including a plurality of primer sets, the kit can be used to detect a plurality of target genes. For example, the kit can target a plurality of disease-associated genes that can be detected from the same sample. More specifically, when targeting genes of infection causing microbes, the kit can be designed to include primer sets that can specifically detect *Staphylococcus aureus, Staphylococcus epidermidis, Pseudomonas aeruginosa, Enterococcus faecalis, Escherichia coli*, and the like. Preferably, the target genes of such infection causing microbes are drug-resistant genes or drug-sensitive genes.

In the case where the target is a set of marker genes for cancer, the kit can be designed to include primer sets that can specifically detect p53, MDM2, H-ras, K-ras, N-ras, APC, Myc, HER2/neu, BRCA1, BRCA2, erbB, src, fos, jun, raf, fes, erb-A, fms, sis, Rb, WT1 and the like. In the case where the target is a set of genetic disease-associated genes, the kit can be designed to include primer sets that can specifically detect, for example, xeroderma pigmentosum-associated genes (XPA, XPB, XPC, XPD, XPE, XPF/ERCC1, XPV), familial colon and rectum carcinoma-associated genes (APC), Alzheimer's disease-associated gene (apoE4), coronary disease-associated gene (apoE2), Von Hippel-Lindau disease-associated gene (VHL), and muscular dystrophy-associated gene (dystrophin).

The applicable fields of the present kit cover all those described in the [1. (5) Applicable Fields of a Nucleic Acid Detection Method of the Present Invention] section. The present kit is applicable to all conventional diagnoses known as gene diagnoses, and the applicable fields of the present kit are not just limited to the examples described above.

The following will describe the present invention in more detail by way of Examples. It should be appreciated, however, that the present invention is not limited to the following description.

Examples 1

Detection of Nucleic Acid Using Phagocytic Sample

[Sample Preparation]

First, brain heart infusion (BHI) medium (DIFCO) was inoculated with foreign microbes, which included *Staphylococcus aureus* (hereinafter "SA", ATCC 126000), *Staphylococcus epidermidis* (hereinafter, "SE", ATCC 14990), *Pseudomonas aeruginosa* (hereinafter "PA", ATCC 10145), *Enterococcus faecalis* (hereinafter "EF", ATCC 19433), and *Escherichia coli* (hereinafter "EC", ATCC 11775). The cells were cultured for 8 hours or longer at 37° C.

Each culture was centrifuged for 10 minutes (2,000×g) at 4° C. and cells were collected. After removing the supernatant, the pellets were suspended in 5 mL PBS, and then centrifuged for another 10 minutes (2,000×g) at 4° C. The cells were collected and suspended in 5 mL PBS, and then diluted in PBS to prepare a 15 mL microbial solution, which had a turbidity of 0.01 to 0.03 (OD=600 nm) as adjusted by an absorption spectrometer. Each microbial solution was placed in a culture flask (175 cm$^2$), and allowed to stand for about 30 minutes at room temperature.

Fifty mL of heparin-supplemented healthy human blood was collected, and a reagent for separating blood (prepared by dissolving 225 mg of sodium chloride and 1.5 g of dextran (MW 200,000 to 300,000) in sterilized pure water and adjusting the volume to 25 mL) was added to the blood at the ratio of about 4:1. The mixture was allowed to stand for 30 minutes at 37° C. (20° C. to 40° C.) and the fraction of white blood cell was removed. The white blood cell fraction was placed in PBS to prepare a 50 mL solution of white blood cells.

The supernatant of the microbial solution in the culture flask was gently removed, and 10 mL of the white blood cell fraction diluted in PBS was added to each flask. The mixture was allowed to stand for about 10 minutes at room temperature. After removing the supernatant in the flask, the white blood cells adhering to the bottom of the flask were collected into a 15 mL centrifuge tube with 10 mL of PBS containing 0.02% EDTA. The solution was centrifuged for 10 minutes (140×g to 180×g) at 4° C. and the white blood cells were collected. When the white blood cells contained red blood cells, the precipitate of white blood cells was gently suspended in 1 mL of sterilized pure water to hemolyze, and after isotonization with 14 mL PBS, centrifugation was performed for another 10 minutes (140×g to 180×g) at 4° C. to collect the white blood cells.

The white blood cells were suspended in PBS, and the number of cells was adjusted to $1\times10^4$ cells/μL to $5\times10^4$ cells/μL based on the cell count of a hemocytometer. The samples so obtained were designated as phagocytic samples and used in the Examples.

[Sample Fixing Step]

Five μL of each phagocytic sample was smeared in the wells of TopYield strips (NUNC: 248909) used as a support, and the samples were air-dried. Then, 100 μL of 75% ethanol was added to each well to fix and desalinate the cells for 5 minutes. After removing the 75% ethanol, the samples were air-dried with a thermal cycler.

[Nucleic Acid Amplifying Step]

Amplification of target nucleic acid was performed by Nested-PCR. First, each well fixing the phagocytic sample was supplemented with PCR reagents (TaKaRa Ex Taq (5 units/μL): 0.5 μL (final 2.5 U), 10× Ex Taq Buffer: 5 μL, dNTP mixture (2.5 mM each): 4 μL, 2 kinds of primers for each bacterial cell line: 0.4 μM, sterilized pure water: up to 50 μL). The following primers were used for the first run:

SA Identifying Primers: SA1T (SEQ ID NO: 1) and SA1B (SEQ ID NO: 2)

SA1T:
5'-GAGGATGCAGCGAATTAAACAACGTACTGCTGTTCAACGC-3'

SA1B:
5'-AATGAAACTTTACCAACAATTTGGTCTTCATCAATGAGGC-3'

SE Identifying Primers: SE1T (SEQ ID NO: 5) and SE1B (SEQ ID NO: 6)

SE1T:
5'-ACTGGAATAATCATTGGTATTATTGCTTTAATTCTAGTAA-3'

SE1B:
5'-CTAACAAAATCTAAGTAGAGTTTCAGGAATTTTTCTGGTT-3'

PA Identifying Primers: PA1T (SEQ ID NO: 9) and PA1B (SEQ ID NO: 10)

PA1T:
5'-ACCTTGCCGATGATCAGGTCGAGCAGCAGCAGTTCCGCCG-3'

PA1B:
5'-GTGTTCACCGGCTCCACCGAGGTCGGCAAGTACTTCATGC-3'

EF Identifying Primers: EF1T (SEQ ID NO: 13) and EF1B (SEQ ID NO: 14)

EF1T:
5'-CTTTTGCTAGTTCATGTTTATTGATTTTTCGTTCGATTAT-3'

EF1B:
5'-TACCATTTCTTGCATGCTCATTTCTCCTTACTACTGAAAC-3'

EC Identifying Primers: EC1T (SEQ ID NO: 17) and EC1B (SEQ ID NO: 18)

EC1T:
5'-CATTTGTGAATGAGATGCACTGACTAAATCAATTGGCCCC-3'

EC1B:
5'-CCGAGATGGGCTTCACCTGTCTGCGTATTTCCATTGCCTG-3'

As the thermal cycler, the GeneAmp PCR System9700 (PE Applied Biosystems) was used. PCR was performed with the following cycling parameters: retention at 94° C. for 1 minute; 30 cycles consisting of 94° C. for 1 minute, and 68° C. for 3 minutes; and retention at 72° C. for 1 minute.

For the second run, a 5 µL solution of the first run was placed in a PCR tube supplemented with the PCR reagents of the foregoing compositions. The following primers were used for the second run:

SA Identifying Primers: SA2T (SEQ ID NO: 3) and SA2B (SEQ ID NO: 4)

```
SA2T:   5'-TGTTCAACGCTTGATTAGTTTTATT-3'
SA2B:   5'-TCAATGAGGCCAAACGCACGGCTAT-3'
```

SE Identifying Primers: SE2T (SEQ ID NO: 7) and SE2B (SEQ ID NO: 8)

```
SE2T:   5'-ATTCTAGTAATTATGCAAGGGTTTC-3'
SE2B:   5'-TTTTCTGGTTCCTCGATATGTGGTG-3'
```

PA Identifying Primers: PA2T (SEQ ID NO: 11) and PA2B (SEQ ID NO: 12)

```
PA2T:   5'-AGTTCCGCCGAGAGGGCGAACATCG-3'
PA2B:   5'-TACTTCATGCAGTATTCCGCGCAAT-3'
```

EF Identifying Primers: EF2T (SEQ ID NO: 15) and EF2B (SEQ ID NO: 16)

```
EF2T:   5'-GTTCGATTATCCCACAAGATTATAT-3'
EF2B:   5'-CTACTGAAACATCGTCTTAAAAAAA-3'
```

EC Identifying Primers: EC2T (SEQ ID NO: 19) and EC2B (SEQ ID NO: 20)

```
EC2T:   5'-AATTGGCCCCCAACTGGTGTACCCC-3'
EC2B:   5'-CCATTGCCTGGGCGCGAATTTTCCC-3'
```

As the thermal cycler, the GeneAmp PCR System9700 (PE Applied Biosystems) was used as in the first run. PCR was performed with the following cycling parameters: retention at 94° C. for 1 minute; 30 cycles consisting of 94° C. for 1 minute, and 68° C. for 1 minutes; and retention at 72° C. for 1 minute.

[Determining Step]

The amplified PCR products were separated by 1% agarose gel electrophoresis (Agarose-RE for $\geq$1 Kbp fragment, for Restriction and Ligation (nacalai tesque)), and were stained by ethidium bromide. The presence or absence of amplification of the target nucleic acid was confirmed by comparing with the result of PCR that was performed with the same primers and using each bacterial cell line as a template.

[Results]

Figure 2:
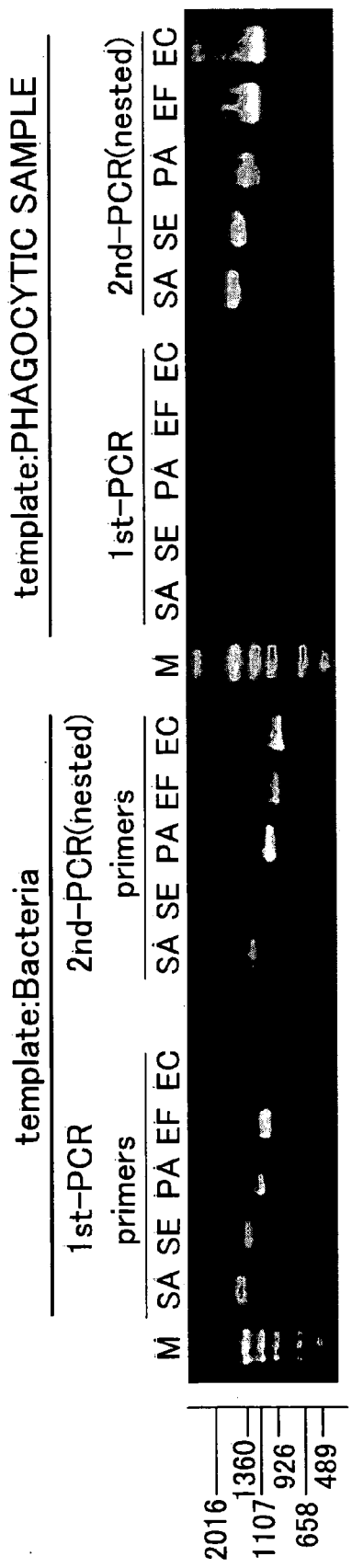
FIG. 2 is an electrophoretic image showing microbes phagocytosed by the white blood cells, as detected by a nucleic acid detection method of the present invention performed on phagocytic cells.

FIG. 2 shows the results. The left-hand side shows the result of PCR that was performed by using each bacterial cell line as a template. The right-hand side shows the result where a nucleic acid detection method of the present invention was used to amplify the target nucleic acid of each bacterial cell line of the phagocytic samples. In FIG. 2, "M" indicates molecular weight marker, and the figures at the left end indicate molecular weight (bp). As is clear from FIG. 1, the second run ($2^{ND}$-PCR (nested)) for the phagocytic samples yielded the same band positions as the second run ($2^{ND}$-PCR (nested)) that used each bacterial cell line as a template. The results therefore showed that the target nucleic acids were actually detected.

Example 2

Determination of Causative Bacteria from Patients with Sepsis

[Sample Preparation]

Five mL of blood was collected from patients suspected to have sepsis, and heparin was added thereto (heparin-supplemented blood). Then, a reagent for separating blood (prepared by dissolving 225 mg of sodium chloride and 1.5 g of dextran (MW 200,000 to 300,000) in sterilized pure water and adjusting the volume to 25 mL) was added to the blood at the ratio of about 4:1, and the mixture was allowed to stand for 30 minutes at 37° C. (20° C. to 40° C.) and the fraction of white blood cell was removed. The solution was then centrifuged for 10 minutes (140×g to 180×g) at 4° C. and the white blood cells were collected. When the white blood cells contained red blood cells, the precipitate of white blood cells was gently suspended in 1 mL of sterilized pure water to hemolyze, and after isotonization with 14 mL PBS, centrifugation was performed for another 10 minutes (140×g to 180×g) at 4° C. The white blood cells were collected and suspended in 150 µL of PBS. The samples so obtained were designated as clinical samples and used in the Example.

[Fixation of Samples]

Five µL of each sample was smeared in the wells of TopYield strips (NUNC: 248909) used as a support, and the samples were air-dried. Then, 100 µL of 75% ethanol was added to each well to fix and desalinate the cells for 5 minutes. After removing the 75% ethanol, the samples were air-dried at 42° C. with a thermal cycler.

[Pre-Treatment of Samples (Nucleic Acid Exposing Step)]

Ten µL of enzyme reagents (1 mL of sterilized pure water dissolving and adjusting: 125 µg of saponin; 125 nL of t-octylphenoxypolyethoxyethanol (specific gravity 1.068 to 1.075 (20/4° C.), pH (5 w/v %) 5.5 to 7.5); 50 units of N-acetylmuramidase (SEIKAGAKU CORPORATION); 5000 units of lysozyme (SEIKAGAKU CORPORATION); and 5 units of lysostaphin (SIGMA). Using a thermal cycler, the samples were then treated for 10 minutes at 37° C., and for another 10 minutes at 95° C., so as to deactivate the enzymes and air-dry the samples.

One unit of N-acetylmuramidase was defined as the enzyme activity that lyses 1 µg of heat-treated cells of S. salivarius IF03350 in 1 minute (37° C., pH 7.0). One unit of lysozyme was defined as the enzyme activity that lowers the absorption of M. luteus at 540 nm by 0.001 in 1 minute (35° C., pH 6.2). One unit of lysostaphin was defined as the enzyme activity that lowers the absorption of S. aureus at 620 nm from 0.240 to 0.125 in 10 minutes (37° C., pH 7.5).

[Nucleic Acid Amplifying Step]

Amplification of target nucleic acid was performed by Nested-PCR. First, each well fixing the sample was supplemented with PCR reagents (TaKaRa LA Taq: 0.2 µL, 10×LA Taq Buffer: 2 µL, 25 mM MgCl$_2$: 2 µL, dNTP mixture (2.5 mM each): 3.2 µL, 2 kinds of primers for each bacterial cell line: 0.16 µM each, adjusted to 20 µL with sterilized pure water).

For the first run, the primers used in Example 1 were used. SA identifying primers SA1T (SEQ ID NO: 1) and SA1B (SEQ ID NO: 2). SE identifying primers SE1T (SEQ ID NO:

5) and SE1B (SEQ ID NO: 6). PA identifying primers PA1T (SEQ ID NO: 9) and PA1B (SEQ ID NO: 10). EF identifying primers EF1T (SEQ ID NO: 13) and EF1B (SEQ ID NO: 14). EC identifying primers EC1T (SEQ ID NO: 17) and EC1B (SEQ ID NO: 18).

As the thermal cycler, the GeneAmp PCR System9700 (PE Applied Biosystems) was used. The first run was performed with the following cycling parameters: retention at 94° C. for 1 minute; 30 cycles consisting of 98° C. for 20 seconds, and 68° C. for 3 minutes; and retention at 72° C. for 5 minutes.

For the second run (Nested-PCR), a 1 μL solution of the first run was placed in a PCR tube supplemented with the PCR reagents of the foregoing compositions. The following primers were used for the second run:

SA Identifying Primers:

```
                                              (SEQ ID NO: 21)
SA3T:  5'-ACTGTTCGTACAAACTTTTGTAATAGTTGGTCATG-3'

(SEQ ID NO: 22)
SA3B:  5'-CTCGCCATCTTTCAAAGTTGGATCCATTGATTCAC-3'
```

SE Identifying Primers:

```
                                              (SEQ ID NO: 23)
SE3T:  5'-GGTATATAAATGACTAAAGGGAGGTGCCAAGATGA-3'

(SEQ ID NO: 24)
SE3B:  5'-GCAATGCACGTACTGCAATTGCACTTTCTTCCGGAG-3'
```

PA Identifying Primers:

```
                                              (SEQ ID NO: 25)
PA3T:  5'-ATTCGATCGTCCTCTTGTTGTCGTTATCGGCATCG-3'

(SEQ ID NO: 26)
PA3B:  5'-TGGTGGAGCGTTCGATCCACGACGAGTTCGTCGAG-3'
```

EF Identifying Primers

```
                                              (SEQ ID NO: 27)
EF3T:  5'-ATCAGGCGTATCCATTATTGGATTAACCACGATTG-3'

(SEQ ID NO: 28)
EF3B:  5'-TTGCTCCTGACGATATTCACGATTCCCTAAAATCC-3'
```

EC Identifying Primes:

```
                                              (SEQ ID NO: 29)
EC3T:  5'-AGATGCGGATTGGGGATCATATTCAGTATGTTGCC-3'

(SEQ ID NO: 30)
EC3B:  5'-GATCACTTCGAACATTACGCCCGCACGGTCTTTAC-3'
```

As the thermal cycler, the GeneAmp PCR System9700 (PE Applied Biosystems) was used as in the first run. PCR was performed with the following cycling parameters: retention at 94° C. for 1 minute; 30 cycles consisting of 98° C. for 20 seconds, and 68° C. for 1 minutes; and retention at 72° C. for 5 minutes.

[Determining Step]

The amplified PCR products were separated by 1% agarose gel electrophoresis (Agarose-RE for ≧1 Kbp fragment, for Restriction and Ligation (nacalai tesque)), and were stained by ethidium bromide. The presence or absence of amplification of the target nucleic acid was confirmed by performing a PCR reaction in which each bacterial cell line corresponding to the primers was used as a template (positive control). PCR was also performed without smearing the samples, so as to confirm there was no non-specific amplification of the target nucleic acid (negative control).

[Results]

FIG. 3 shows the result of electrophoresis. In FIG. 3, the figures at the left end indicate molecular weight (bp). As is clear from FIG. 3, lane 13 and lane 15 showed specific amplification of nucleic acid. Based on this result, it was determined that these clinical samples were infected with SA (*Staphylococcus aureus*) and PA (*Pseudomonas aeruginosa*) (positive result).

Table 1 shows results of experiment that was performed according to the foregoing method to determine causative bacteria in 4 different clinical samples, including the clinical sample 1 described above.

TABLE 1

|  | SA | SE | PA | EF | EC | Blood Culture |
|---|---|---|---|---|---|---|
| Clinical Sample 1 | Positive | Negative | Positive | Negative | Negative | Negative |
| Clinical Sample 2 | Negative | Negative | Positive | Negative | Negative | Negative |
| Clinical Sample 3 | Negative | Negative | Positive | Negative | Negative | Negative |
| Clinical Sample 4 | Positive | Negative | Positive | Negative | Negative | Negative |

The results shown in Table 1 clearly suggest that a nucleic acid detection method according to the present invention is indeed effective in the determination of causative bacteria in patients with sepsis.

Example 3

Detection of Biological Factor (RNA) from Septic Blood Model

[Preparation of Septic Blood Model]

First, brain heart infusion (BHI) medium (DIFCO) was inoculated with a foreign microbe (*Escherichia coli* (hereinafter "EC", ATCC 11775)), and the cells were cultured for 8 hours or longer at 37° C. The cell culture was centrifuged for 10 minutes (2,000×g) at 4° C. and cells were collected. After removing the supernatant, the pellets were suspended in 5 mL PBS, and then centrifuged for another 10 minutes (2,000×g) at 4° C. The cells were collected and suspended in 5 mL PBS, and then diluted in PBS to prepare a 5 mL microbial solution, which had a turbidity of 0.1 to 0.15 (OD=600 nm) as adjusted by an absorption spectrometer. 8 mL of heparin-supplemented healthy human blood was collected, and was placed in two 15 mL centrifuge tube, 4 mL each. Each of the 4 mL heparin-supplemented blood samples was supplemented with 400 µL of microbial solution and PBS, and the mixture was allowed to stand for 3 hours at 37° C. to induce expression of inflammatory cytokine.

Then, a reagent for separating blood (prepared by dissolving 225 mg of sodium chloride and 1.5 g of dextran (MW 200,000 to 300,000) in sterilized pure water and adjusting the volume to 25 mL) was added to the blood at the ratio of about 4:1, and the mixture was allowed to stand for 30 minutes at 37° C. (20° C. to 40° C.) and the fraction of white blood cell was removed. The solution was then centrifuged for 10 minutes (140×g to 180×g) at 4° C. and the white blood cells were collected. When the white blood cells contained red blood cells, the precipitate of white blood cells was gently suspended in 1 mL of sterilized pure water to hemolyze, and after isotonization with 14 mL PBS, centrifugation was performed for another 10 minutes (140×g to 180×g) at 4° C. and the white blood cells were collected. The white blood cells were then suspended in 150 µL of PBS. The sample was designated as septic blood model and used in this Example.

[Fixation of Sample]

Five µL of the sample was smeared in the wells of TopYield strips (NUNC: 248909) used as a support, and the sample was air-dried. Then, 100 µL of 75% ethanol was added to each well to fix and desalinate the cells for 5 minutes. After removing the 75% ethanol, the sample was air-dried at 42° C. with a thermal cycler.

[Pre-Treatment of Sample]

Ten µL of DNase (0.1 unit/µL of DNaseI, RNase-free (Roche Diagnostics GmbH), Tris-HCl 10 mM, MgCl$_2$ 10 mM, DTT 1 mM, and sterilized distilled water). Using a thermal cycler, the sample was then treated for 10 minutes at 37° C., so as to degrade the genomic DNA of the white blood cells. The sample was treated for another 10 minutes at 37° C. to deactivate the enzyme and air-dry the wells.

One unit of enzyme was defined as the enzyme activity that increases the absorption at 260 nm in 1 minute (25° C., pH 5.0), when calf thymus DNA was used as a substrate.

[Nucleic Acid Amplifying Step]

Amplification of target nucleic acid was performed by RT-PCR. The procedure began with a reverse transcription (RT) reaction, for which the super script fast strand system (for RT-PCR) (Invitrogen) was used. Each well fixing the sample was supplemented with 1 µL of Oligo(dT)12-18 (0.5 µg/µL) and 9 µL of sterilized distilled water. The mixture was treated for 10 minutes at 70° C., and was allowed to stand for 1 minute at 4° C. The mixture was further supplemented with 2 µL of 10×PCR buffer [200 mM Tris-HCl (pH 8.4), 500 mM KCl], 2 µL of 25 mM MgCl$_2$, 1 µL of 10 mM dNTP mix, and 2 µL of 0.1 M DTT, and was allowed to stand for 5 minutes at 25° C. Thereafter, 1 µL of SuperScript II RT (50 units) was added, and following treatment for 10 minutes at 25° C., 50 minutes at 42° C., and 15 minutes at 70° C., the mixture was allowed to stand for 5 minutes at 4° C. After the revere transcription reaction, 1 µL of *E. coli* RNaseH (2 units/µL) was added and the mixture was treated for 20 minutes at 37° C. to completely degrade RNA.

PCR reaction was performed by adding 2 µL of RT solution into a PCR tube that contained PCR reagents in the following amounts per well (TaKaRa LA Taq: 0.2 µL, 10×LA Taq Buffer: 2 µL, 25 mM MgCl$_2$: 2 µL, dNTP mixture (2.5 mM each): 3.2 µL, IL6 identifying primers: 0.16 µM each, adjusted to 20 µL with sterilized pure water).

For the PCR reaction, Interleukin 6 (IL6) primers were used.

```
                                          (SEQ ID NO: 31)
IL6-T: 5'-ATGAACTCCTTCTCCACAAGCGCCTTCGG-3'

(SEQ ID NO: 32)
IL6-B: 5'-ATTCTTTGCCTTTTTCTGCAGGAACTGGAT-3'
```

As the thermal cycler, the GeneAmp PCR System9700 (PE Applied Biosystems) was used. The PCR was performed with the following cycling parameters: retention at 94° C. for 1 minute; 50 cycles consisting of 94° C. for 30 seconds, 55° C. for 30 seconds, and 72° C. for 30 seconds; and retention at 72° C. for 5 minutes.

[Determining Step]

The amplified PCR products were separated by 2% agarose gel electrophoresis (Agarose-RE for ≧1 Kbp fragment, for Restriction and Ligation (nacalai tesque)), and were stained by ethidium bromide. Amplification of target nucleic acids was confirmed by the presence of specific bands in electrophoresis.

[Results]

FIG. 4 shows results of electrophoresis. In FIG. 4, the figures at the left end indicate molecular weight (bp). As shown in FIG. 4, lane 3 had specific amplification of nucleic acid with IL6, demonstrating that a nucleic acid detection method of the present invention has indeed detected the increased expression level of IL6 in blood infected with *E. coli*.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

A nucleic acid detection method according to the present invention includes: a sample fixing step of fixing a cell-containing sample on a support; a nucleic acid amplifying step of amplifying sample's nucleic acids on the support; and a determining step of determining whether the amplified nucleic acids contain a target nucleic acid. The method does not require the step of extracting nucleic acids from a sample. There accordingly will be almost no loss of nucleic acids due to the extraction procedure. Further, the method is able to detect the target nucleic acid, as long as the sample contains it in a sufficient amount to provide a template for amplification, even when the amount of target nucleic acid contained in the sample is trace. This advantageously improves reproducibility and detection accuracy. Further, since the nucleic acid extracting step is not required, the method offers a simple procedure and quickly yields results.

In a nucleic acid detection method according to the present invention, the sample is fixed on a support. In this way, the amplification inhibiting substances contained in the extracellular domain can easily be removed even when the sample contains these substances. Accordingly, there will be no lowering of detection sensitivity due to reduced amplification efficiency.

In a nucleic acid detection method according to the present invention, the sample is fixed on a support and the nucleic acids are amplified on the support. Thus, there is no need to transfer the sample into a separate container such as a PCR tube. There accordingly will be no loss of nucleic acid due to transfer of the sample, and there is no lowering of detection sensitivity. Further, the method offers a simple procedure and quickly yields results.

In a nucleic acid detection method according to the present invention, detection is made after nucleic acids have been amplified. Accordingly, there is no difficulty in detecting the target nucleic acid even when it is contained only in a trace amount. This advantageously improves reproducibility and detection accuracy. Further, since the method does not employ any unique procedure, various types of known detection methods can be suitably selected and used in the nucleic acid detection method of the present invention. Further, no skill is required to yield results.

A gene detecting kit according to the present invention uses a nucleic acid detection method of the present invention to detect a target gene in a sample. By using the kit, a nucleic acid detection method of the present invention can be performed very conveniently and quickly.

As described above, the present invention is applicable to all fields of diagnoses known as genetic diagnoses. The present invention can therefore be used in a wide range of bio-industries, including medicine, pharmaceuticals, and reagents. Further, when used in clinical testing in medicine, the present invention can help choose the right course action in the treatment of disease. Further, the present invention can be used for the basic research in bio-related fields. Contribution of the present invention in the development of biology is greatly anticipated in this regard.

The invention claimed is:

1. A nucleic acid detection method comprising:
   fixing a cell-containing sample directly on divided compartments of a support by dry fixation, wherein the fixation consists of:
   i) smearing the sample in the divided compartments,
   ii) air-drying the smeared samples,
   iii) adding 75% ethanol to each compartment, and
   iv) air-drying the samples with a thermal cycler after removing the 75% ethanol;
   pre-treating the sample to enable amplification of nucleic acids contained in the sample;
   performing PCR by placing a PCR mixture, containing primers for amplifying a target nucleic acid, into the compartments of the support; and
   determining whether amplified nucleic acids existing in a PCR solution outside of the fixed cell sample contain the target nucleic acid.

2. The nucleic acid detection method as set forth in claim 1, wherein the pre-treating step is performed by one or more methods selected from the group consisting of a detergent treatment method, an enzyme treatment method, and a heat treatment method.

3. The nucleic acid detection method as set forth in claim 1, wherein the amplified nucleic acids are labeled in the step of performing PCR.

4. The nucleic acid detection method as set forth in claim 3, wherein, in the determining step, the nucleic acids amplified and labeled in the step of performing PCR are used as probes for complementary hybridization with known gene fragments.

5. The nucleic acid detection method as set forth in claim 4, wherein the known gene fragments are fixed on the support in advance.

6. The nucleic acid detection method as set forth in claim 3, wherein, in the determining step, the nucleic acids amplified and labeled in the step of performing PCR are used as probes for a DNA microarray.

7. The nucleic acid detection method as set forth in claim 1, wherein the sample originates in biological sources.

8. The nucleic acid detection method as set forth in claim 7, wherein the biological sample originates in humans.

9. The nucleic acid detection method as set forth in claim 1, wherein the support with the divided compartments is shaped to fit a gene amplifier for PCR.

10. The nucleic acid detection method as set forth in claim 1, wherein, in the determining step, the target nucleic acid is detected by electrophoresis.

11. A nucleic acid detection method comprising:
    fixing a cell-containing sample directly on divided compartments of a support by dry fixation, wherein the fixation consists of:
    i) smearing the sample in the divided compartments,
    ii) air-drying the smeared samples,
    iii) adding 75% ethanol to each compartment, and
    iv) air-drying the samples with a thermal cycler after removing the 75% ethanol;
    pre-treating the sample to enable amplification of nucleic acids contained in the sample;
    performing PCR by placing a PCR mixture, containing primers for amplifying a target nucleic acid, into the compartments of the support;

detecting amplified nucleic acids existing in a PCR solution outside of the fixed cell sample; and determining whether the amplified nucleic acids are the target nucleic acid.

12. The nucleic acid detection method as set forth in claim 11, wherein the pre-treating step is performed by one or more methods selected from the group consisting of a detergent treatment method, an enzyme treatment method, and a heat treatment method.

13. The nucleic acid detection method as set forth in claim 11, wherein the amplified nucleic acids are labeled in the step of performing PCR.

14. The nucleic acid detection method as set forth in claim 13, wherein, in the determining step, the nucleic acids amplified and labeled in the step of performing PCR are used as probes for complementary hybridization with known gene fragments.

15. The nucleic acid detection method as set forth in claim 14, wherein the known gene fragments are fixed on the support in advance.

16. The nucleic acid detection method as set forth in claim 13, wherein, in the determining step, the nucleic acids amplified and labeled in the step of performing PCR are used as probes for a DNA microarray.

17. The nucleic acid detection method as set forth in claim 11, wherein the sample originates in biological sources.

18. The nucleic acid detection method as set forth in claim 17, wherein the biological sample originates in humans.

19. The nucleic acid detection method as set forth in claim 11, wherein the support with the divided compartments is shaped to fit a gene amplifier for PCR.

20. The nucleic acid detection method as set forth in claim 11, wherein, in the determining step, the target nucleic acid is detected by electrophoresis.

* * * * *